Figure 1:
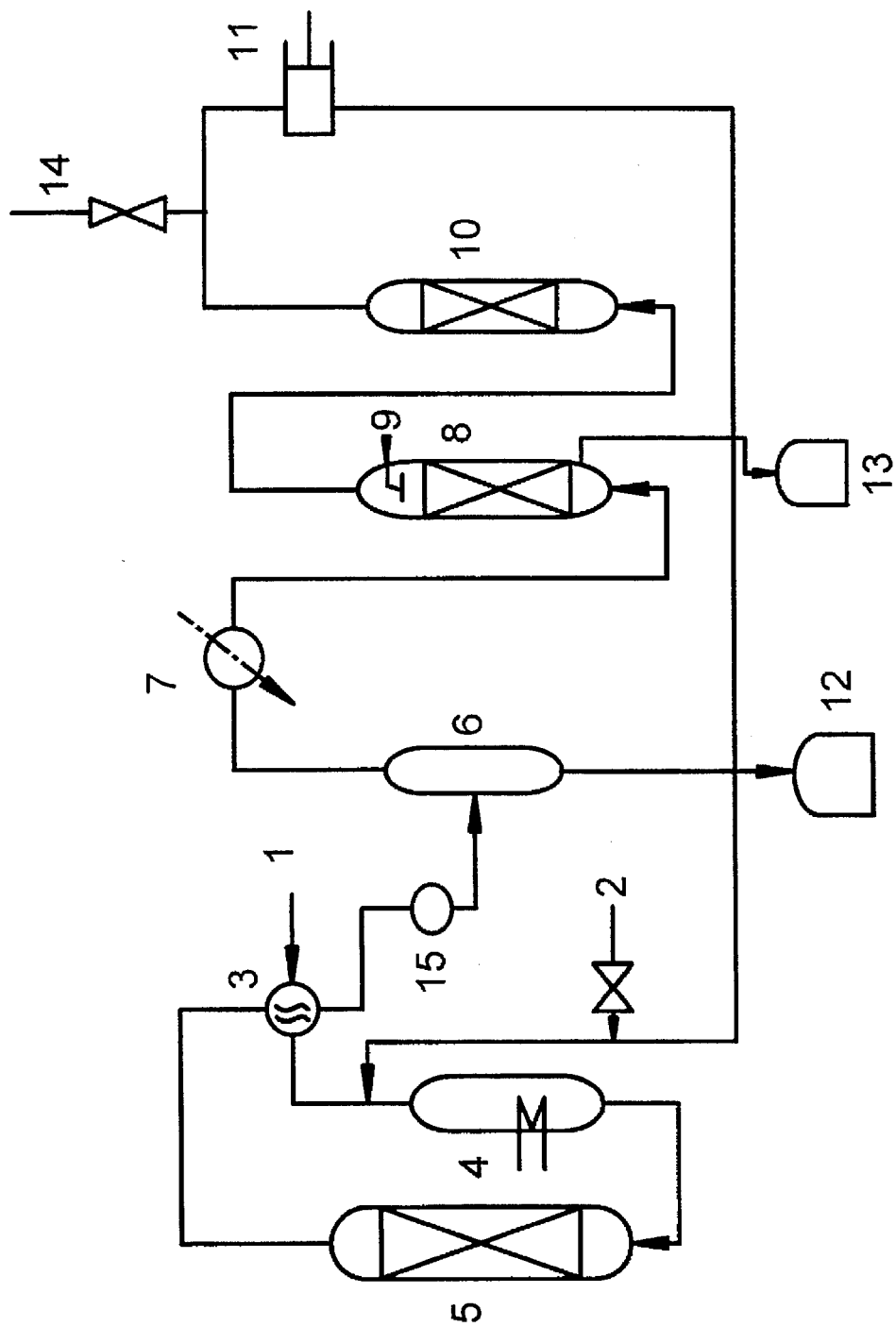

United States Patent [19]

Liu et al.

[11] Patent Number: 5,648,538

[45] Date of Patent: Jul. 15, 1997

[54] PROCESS FOR PREPARING DIARYLAMINES FROM ARYLAMINES

[75] Inventors: Xiusen Liu; Huarong Zhu; Fubin Ai; Lizhi Song; Zhihui Lu; Xuewei Hou, all of Liaoning, China

[73] Assignees: Fushun Research Institute of Petroleum and Petrochemicals, Liaoning; China Petrochemical Corp., Beijing, both of China

[21] Appl. No.: 496,520

[22] Filed: Jun. 29, 1995

[30] Foreign Application Priority Data

Jun. 29, 1994 [CN] China ................................. 94107296.7

[51] Int. Cl.$^6$ ................................................. C07C 209/00
[52] U.S. Cl. ........................ 564/307; 564/315; 564/433; 564/434; 564/435
[58] Field of Search ................................. 564/307, 315, 564/433, 434, 435

[56] References Cited

U.S. PATENT DOCUMENTS

| 3,118,944 | 1/1964 | Addis ................................. 564/435 |
| 3,944,613 | 3/1976 | Naramoto et al. ..................... 564/435 |
| 4,454,348 | 6/1984 | Aiken et al. .......................... 564/435 |
| 4,814,504 | 3/1989 | Malz ................................... 564/435 |

FOREIGN PATENT DOCUMENTS

| 53-79824 | 7/1978 | Japan . |
| 1439838 | 6/1976 | United Kingdom . |

*Primary Examiner*—Richard L. Raymond
*Attorney, Agent, or Firm*—Burns, Doane, Swecker & Mathis LLP

[57] ABSTRACT

A process for preparing diarylamines in high yield, in which diarylamines are prepared from arylamines in the presence of a solid acid catalyst. The solid acid catalyst with good stability and regeneration ability consists of H-type beta zeolite and active alumina, the ratio of $SiO_2/Al_2O_3$ in the zeolite is 20~100, and the content of active alumina is 10%~70% (wt).

4 Claims, 1 Drawing Sheet

PROCESS FOR PREPARING DIARYLAMINES FROM ARYLAMINES

This invention relates to a process for preparing diarylamines from arylamines in the presence of solid acid catalyst, more particularly to a process for preparing diphenylamine from aniline.

There are many processes for preparing diarylamines from arylamines reported in literature, and they are mainly gas phase process and pressure liquid phase process, but all these processes have many vital shortcomings. For example, GB 1,439,838 and U.S. Pat. No. 3,118,944 disclose a gas phase process for preparing diphenylamine from aniline by using solid acid catalyst such as $Al_2O_3$ or $TiO_2$—$Al_2O_3$, in which process, the reaction temperature is above 450° C., the product yield is low, and the catalyst used is of short duration and needs regenerating frequently in industrial application.

U.S. Pat. No. 4,814,504 discloses a gas phase process for preparing diphenylamine from aniline by using $BF_3$ or $Al_2O_3$ treated with aniline—$BF_3$ as catalyst. Although its activity is somewhat higher than that of $Al_2O_3$, the conversion rate of aniline is still not high, and it is not assured that the catalyst possesses prolonged duration.

JP 7879824 discloses a gas phase process for preparing diphenylamine, in which $Al_2O_3$ or $Al_2O_3$ containing boron is used as catalyst and addition of an amount of water into the starting material anilines can prolong the duration of the catalyst. However, the reaction temperature is still as high as 460° C., and this enables the product more difficult to be seperated and increases the production cost.

U.S. Pat. No. 4,454,348 discloses a gas phase process for preparing diphenylamine from aniline, in which $Al_2O_3$ containing $SiO_2$ is used as catalyst and addition of ammonia into the starting material can increase the recovery of the pruduct and selectivity but this is only suitable to the case of low conversion rate of aniline. When the conversion rate of aniline is high, the addition of ammonia will inhibit the production of diphenylamine.

U.S. Pat. No. 3,944,613 describes a pressure liquid phase process for preparing diphenylamine, in which $SiO_2$—$Al_2O_3$ is used as catalyst and reaction temperature is 320°~370° C. However the conversion rate of aniline is low, and there are many by-products.

Alternatively, there are a number of pressure liquid phase processes for preparing diarylamines from arylamines by using mineral acid or lewis acid such as $AlCl_3$, HCl, $BF_3$ and the like as catalyst, but there are problems concerning eguipment corrosion and environmental pollution besides low product recovery and more by-products.

Accordingly, object of this invention is to provide a process for preparing diarylamines from arylamines with high conversion rate, less by-product, low production cost and without problems concerning eguipment corrosion and environmental pollution.

The present inventors consider that the reason why the processes in the prior art have various vital shortcomings is mainly no good catalyst which is particalarly suitable for preparing diarylamines from arylamines. Therefor, the present inventors concentrate their attention on studying the catalyst used in prepaing diarylamines from arylamines, and finally they have surprisedly found a catalyst with high activity, good stability and long duration, thus finished the present invention.

The present invention provides a process for preparing diarylamines from arylamines. Characterized in that a compound of formula (I) is reacted with a compound of formula (II) in the presence of a solid acid catalyst at the temperature of 250°~450° C., to obtain diarylamine compound of formala (III):

 (I)

 (II)

 (III)

Wherein

R and $R_1$ are identical or different and each represents H, $C_{1~12}$ alkyl, $C_{1~12}$alkoxy, $C_{1~12}$alkoxy $C_{1~12}$alkyl, hydroxy $C_{1~12}$alkyl, phenyl, phenyl $C_{1~12}$alkyl, hydroxy, amino or nitro;

Ar represents phenyl;

n represents a integer of 0–5, when n is 1, the substitutes represented by R and $R_1$ can be in ortho-, meta- or para-position relative to the amino in benzene ring; and when n is equal to or greater than 2, R and $R_1$ respectively represent two or more substitutes which are identical or different.

The term "$C_{1~12}$alkyl" herein used refers to linear or branched alkyl having 1~12 carbon atoms, such as methyl, ethyl, propyl, isopropyl, butyl, isobutyl, pentyl, hexyl, octyl and the like.

The term "$C_{1~12}$alkoxy" herein used refers to hydroxy which is substituted by the above linear or branched $C_{1~12}$alkyl, such as methoxy, ethoxy, propoxy, isopropoxy, butoxy, isobutoxy, hexyloxy and dodecyloxy and the like.

The catalyst used in the process according to the present invention consists of H-type beta zeolite and active alumina, wherein the molecular ratio of H-type beta zeolite to $Al_2O_3$ is 20~100, preferably 30~70, and the content of active alumina is 10%~70% (wt), preferably 20%~50% (wt).

The catalyst used in the present invention can be prepared by conventional methods, for example, by mixing H-type beta zeolite with $Al(OH)_3$powder, with the amount of $Al(OH)_3$ added being calculated on the basis of the γ-$Al_2O_3$ content in the catalyst of 10%~70% (wt); adding suitable amount of dilute nitric acid; mixing and Kneading the mixture homogeneously; then extruding the homogeneous mixture by extruder to form strips; drying the strips at 60° C. for 4–8 hours, and at 116°~120° C. for 4~8 hours; and calcining the strips at 500°~700° C. for 8–16 hours, thus obtaining the catalyst according to the present invention.

The process according to the present invention can be used in both of batch reaction process and continuous reaction process.

In the case of batch reaction process, for example in autoclave, the reaction temperature is 250°~400° C., and the reaction pressure is equal to or higher than the pressure at which the arylamine to take part in the reaction can be maintained in liquid phase state.

In the case of continuous reaction process, the reaction can be carried out in gas phase or liquid phase, preferably in liquid phase.

The temperature of gas phase reaction is 280°~450° C., preferably 340°~430° C., more preferably 360°~400° C.; the reaction pressure is equal to or higher than mormal pressure, preferably 0.1–0.5 MPa, more preferably 0.1–0.2 MPa; and the space velocity is 0.02–1.0 $h^{-1}$ (w), preferably 0.05–0.5 $h^{-1}$ (w), more preferably 0.1–0.3 $h^{-1}$ (w).

The temperature of liquid phase reaction is 250°~400° C., preferably 280°~360° C., more preferably 300°~340° C.; the reaction pressure is 0.5~4.5 MPa, preferably 1.0–4.0 MPa, more preferably 2.5~3.5 MPa; and the space veloaty is 0.05~1.0 $h^{-1}$ (w), preferably 0.1~0.5 $h^{-1}$ (w), more preferably 0.2~0.4 $h^{-1}$ (w).

In contimeous reaction process, carrier gas is optionally passed into the reaction. The carrier gas used in the present process includes hydrogen, nitrogen, other inert gas, and their mixture. Hydrogen is preferably used because hydrogen can protect the present catalyst to some extent.

FIG. 1 is a schematic diagram of the process flow of a prefered example in the application of the present process.

The present invention will be explained in detail in reference to FIG. 1. below.

The starting material arylamine is withdrawn from line 1, and made to exchange heat in heat-exchanger 3, then fed into heating oven 4 together with the circulating hydrogen (including the supplemented fresh hydrogen). The volume ratio of hydrogen to arylamine is 20~600. After having heated through heating oven 4, arylamine and hydrogen flow into reactor 5, wherein the reaction temperature is 250°~400° C., and the reaction pressure is 0.5~4.5 MPa. The flow from reactor 5 exchanges heat with the starting material arylamine in heat-exchanger 3, and after cooled in cooler 15, flows into separator 6 in which the temperature is between 160° and 190° C., and the pressure is the reaction pressure. After being separated, the liquid phase containing arylamine, diarylamine and a small amount of other components flows into storage tank 12; while the gas phase part is cooled to 40°~70° C. in cooler 7 and then flows from the bottom of the column into water-washing column 8, where it contacts counter-current-wise with the water added from line 9 at the top of the column. The aqueous ammonia resulted from ammonia absorbed by water flows from the bottom of the column into storage tank 13. the hydrogen deammoniated by washing with water flows from the top of the column into drying column 10. The dried hydrogen is used to circulate from circulating compressor 11 to heating oven 4. In the FIGURE, valve 14 is one used to evacuate hydrogen, and valve 2 is one used to supplement fresh hydrgen.

In comparison with the prior art, because of the use of H-type beta zeolite/Al$_2$O$_3$ solid acid catalyst with high activity, good stability and prolonged duration in the present invention, the conversion rate of arylamine is high, the by-aroducts become less, and the production cost is low.

The following examples are provided to illustrate the present invention in detail, but not to limit the scope of the present invention.

EXAMPLE 1

A. Preparation of Catalyst 70 g H-type beta zeolite with molecular ratio of SiO$_2$/Al$_2$O$_3$ of 47.5 was mixed with 20 g industrial Al(OH)$_3$ powder, and then 20 ml 10% (V) diluted nitric acid was added thereto. The mixture was mixed and kneaded homogeneously, and molded by a extruder into strips (2 mm in diameter). The strips were dried at 60° C. for 4 hours, then at 120° C. for 4 hours, and calcined at 600° C. for 8 hours, wherefore the catalyst of the present invention was obtained.

B. Preparation of diphenylamine

To a 200 ml autoclave was added 50 g the above-obtained catalyst (particle size 40~80 mesh), then added 100 g aniline. The air in the autoclave was displaced with nitrogen for three times. When the pressure rose to 1.0 MPa, heating started. On the temperature reaching at 320° C., the pressure in the autoclave was adjusted to 2.0 MPa with nitrogen. The reaction was carried out for 2.5 hours, then the reaction mixture was cooled and filtered. The product was analyzed by gas chromatography, and the results were given in Table 1 below.

The reaction was carried out in exactly the same process as that mentioned above except that the catalyst of the present invention was replaced by the active alumina catalyst and amorphous silica-alumina catalyst containing 25% alumina which are commonly used in the prior art respectively. The products were also analyzed by gas chromatography and the results were given in Table 1 below.

The data in Table 1 show that the activity of the catalyst of the present invention is apparently superior to that of the active alumina and amorphous silica-alumina catalyst used in the prior art.

TABLE 1

| Catalyst | composition of the liquid phase products (%) | | | | vice yield (%)* |
|---|---|---|---|---|---|
| | aniline | diphenylamine | light component | heavy component | |
| catalyst of the invention | 55.3 | 43.4 | 0.6 | 0.7 | 3.0 |
| active alumina | 74.1 | 25.1 | 0.3 | 0.5 | 3.2 |
| amorphous silica - alumina | 70.0 | 28.4 | 0.7 | 0.9 | 5.6 |

*vice yield = [(light component + heavy component)/Diphenylamine] × 100

EXAMPLE 2

The reaction was conducted in the same manner as in Example 1, except that aniline was replaced by 3-methylaniline. The reaction products were cooled and filtered, and then analyzed by gas chromatography, the contents of the product by weight were as follows: 3,3'-dimethyl diphenylamine 61.6%, 3-methylaniline 46.7%, other components 1.7%.

EXAMPLE 3

The reaction was conducted in the same manner as in Example 1, except that 2-methyl-4-ethylaniline was used to replace aniline and reaction temperature was 340° C. The reaction product was cooled and filtered, then analyzed by gas chromatography. The contents of the products by weight were as follows 2,2'-dimethyl-4,4'-diethyl diphenylamine 20.5%, 2-methyl-4-ethylaniline 77.2%, other components 2.3%.

EXAMPLE 4

The reaction was conducted in the same manner as in Example 1 except that aniline was replaced by 50 g 3-methyl-aniline and 57 g 3-ethylaniline, the reaction product was cooled and filtered, then analyzed by gas chromatography, the contents of the products by weight were as follows: 19.5% of 3,3'-dimethyldiphenylamine; 12.3% of 3,3'-diethyldiphenylamine; 13.9% of 3-methyl-3'-ethyldiphenylamine; 18.8% of 3-methylaniline; 33.7% of 3-ethylaniline; and 1.9% of other components.

EXAMPLE 5-11

The reaction was conducted in the same manner as in Example 1 except that aniline was replaced by the starting materials listed in Table 3 respectively, the reaction results were given in Table 2 below.

TABLE 2

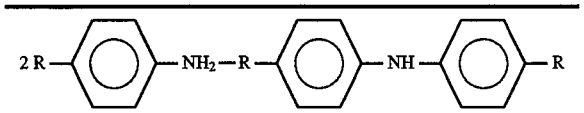

| Example Number | Substitute R | Composition of the reaction products % (wt) | | |
|---|---|---|---|---|
| | | Main product | Starting materials | Other components |
| 5 | *ph- | 12.6 | 86.7 | 1.7 |
| 6 | —OH | 21.9 | 76.8 | 1.3 |
| 7 | —NH$_2$ | 25.4 | 69.9 | 4.7 |
| 8 | —NO$_2$ | 13.8 | 84.3 | 1.9 |
| 9 | CH$_3$CH$_2$O— | 14.3 | 83.6 | 2.1 |
| 10 | *ph-CH$_2$CH$_2$— | 8.9 | 89.9 | 1.2 |
| 11 | (CH$_3$)$_2$CH— | 18.6 | 78.7 | 2.7 |

*ph phenyl.

EXAMPLE 12

The catalyst prepared in Example 1 was cracked into particles (40–60 mesh), and the particles (15 g) were filled into a stainlers steel reactor (12 mm in inner diameter, 650 mm in length). Aniline was pumped to the bottom of the reactor by a metering pump at a feed rate of 11.7 ml/h. The reaction pressure was 2.0 MPa. The reaction product flow from the top of the reactor was cooled and then, collected in a normal-pressure separator, in which the ammonia in gas phase was withdrawn from the top of the separator, and the liquid phase at the bottom was analyzed by gas chromatography to determine its composition, and the results were given in Table 3.

In order to compare with the prior art, the reaction was carried out. in the same process as that described above by using silica-alumina catalyst containing 25% alumina. The liquid phase at the bottom was analyzed by gas chromatography to determine its composition, and the results were given in table 3.

TABLE 3

| Catalyst | Reaction temp. (°C.) | Content composition of the liquid phase products (%) | | | Vice-yield (%) |
|---|---|---|---|---|---|
| | | Aniline | Diphenyl-amine | By-product | |
| Catalyst of the invention | 320 | 83.46 | 16.30 | 0.24 | 1.47 |
| | 345 | 80.24 | 19.40 | 0.36 | 1.86 |
| Silica - alumina catalyst | 320 | 86.1 | 13.5 | 0.4 | 2.96 |
| | 345 | 83.2 | 16.1 | 0.7 | 4.35 |

Table 3 indicates that the activity of the catalyst of the present invention was apparently higher than that of the catalysts in the prior art in the case of liquid phase reaction without carrier gas.

EXAMPLE 13

Test of stability and regeneration ability of the present catalyst 300 ml (222 g) catalyst (particle size 10–26 mesh) prepared in Example 1 was charged to a stainless steel reactor (25 mm in inner diameter, 1.5 m in length). Amiline was fed to the bottom of the reactor at a rate of 80 ml/h, and a small amount of hydrogen was gassed in the reactor at a rate of 10 L/h. The reaction pressure was 3.0 MPa, and the reaction temperature was 320° C. The product flow from the top of the reactor was cooled and then entered separator, hydrogen and ammonia were withdrawn from the top of the separator. The percentage composition of the liquid phase was analyzed by gas chromatography. The reaction was carried out continuously for 1500 hours, then the catalyst was regenerated twice by conventional regeneration method of combustion of the nitrogen-oxygen gas mixture. The results are given in Table 4. As is seen from Table 4, the catalyst according to the present invention possesses not only higher activity and stability, but also good regeneration ability.

TABLE 4

| RUN TIME (hr) | FIRST RUN Composition of Liquid Phase Product (wt %) | | | RUN AFTER FIRST REGENERATION Composition of Liquid Phase Product (wt %) | | | RUN AFTER SECOND REGENERATION Composition of Liquid Phase Product (wt %) | | |
|---|---|---|---|---|---|---|---|---|---|
| | Aniline | Diphenylamine | By-product | Aniline | Diphenylamine | By-product | Aniline | Diphenylamine | By-product |
| 10 | 68.36 | 31.27 | 0.37 | 70.37 | 29.31 | 0.32 | 70.78 | 28.94 | 0.28 |
| 200 | 70.55 | 29.17 | 0.28 | 71.23 | 28.50 | 0.27 | 72.22 | 27.51 | 0.27 |
| 500 | 71.01 | 28.72 | 0.27 | 71.63 | 28.12 | 0.25 | | | |
| 800 | 71.77 | 27.98 | 0.25 | 72.25 | 27.50 | 0.25 | | | |
| 1000 | 73.65 | 26.12 | 0.23 | 73.90 | 25.86 | 0.24 | | | |
| 1200 | 75.35 | 24.43 | 0.22 | 75.47 | 24.31 | 0.22 | | | |
| 1500 | 77.40 | 22.41 | 0.19 | 78.08 | 21.72 | 0.20 | | | |

EXAMPLE 14

The experiment was carried out in the equipment shown in FIG. 4.

50 L β zeolite-Al$_2$O$_3$catalyst (35 kg) was charged into a stainless steel reactor 5 (180 mm in inner diameter, 2.5 m in length) and aniline was fed to the bottom of the reactor 5 at a rate of 10 kg/h, the ratio of hydrogen/aniline (V) being 100~400. The reaction pressure was 4.0 MPa, and the reaction temperature was 300°~320° C. The effluent material from the top of the reactor 5 exchanged heat with the starting material aniline in heat-exchanger 3, cooled in cooler 15 and then flowed into separator 6, in which the pressure was the same as that of the reactor and temperature was controlled at 175° C. The liquid part in the separator entered the storage tank 12, while the gas phase part was cooled to 40°~60° C. by cooler 7 and then entered the bottom of the water-washing column 8, where it contacted counter-current-wise with the water added from line 9, the amount of water added is 5 kg/h, and temperature of water is 15° C. The aqueous ammonia resulted from water and the absorbed ammonia entered storage tank 13, while the deammoniated hydrogen entered drying column 10 which was packed with active charcoal. The dried hydrogen, free from ammonia and water, returned to the reactor 5 through circulating compressor 11. The liquid part in storage tank 12 was analyzed by gas chromatography to determine composition, and the results were given in table 5.

TABLE 5

COMPOSITION OF PRODUCTS AT DIFFERENT TEMPERATURES (%)

| Reaction Temperature (°C.) | Hydron/Aniline (vol) | Liquid Phase Composition of Reaction Product (% wt) | | |
|---|---|---|---|---|
| | | Aniline | Diphenylamine | By-product |
| 300 | 375 | 76.6 | 23.2 | 0.2 |
| 310 | 375 | 75.6 | 24.1 | 0.3 |
| 310 | 250 | 75.2 | 24.6 | 0.2 |
| 310 | 125 | 75.3 | 24.5 | 0.2 |
| 320 | 125 | 73.1 | 26.6 | 0.3 |
| 320 | 100 | 73.5 | 26.2 | 0.3 |
| 330 | 300 | 71.4 | 28.2 | 0.4 |
| 340 | 300 | 69.1 | 30.5 | 0.4 |
| 350 | 300 | 66.8 | 32.7 | 0.5 |

I claim:

1. A process for preparing diarylamines from arylamines, said process comprising reacting a compound of formula (I):

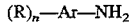  (I)

with a compound of formula (II):

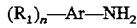  (II)

in the presence of a solid acid catalyst at a temperature between 250° and 450° C. to obtain a diarylamine compound of formula (III):

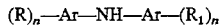  (III)

wherein

R and $R_1$ are identical or different, and each represents $C_{1-12}$ alkyl, $C_{1-12}$ alkoxy, $C_{1-12}$ alkoxy $C_{1-12}$ alkyl, hydroxy $C_{1-12}$ alkyl, phenyl, phenyl $C_{1-12}$ alkyl, hydroxy, amino or nitro;

Ar represents phenyl;

n represents an integer from 0 to 5, when n is 1, R and $R_1$ are in the ortho-, meta- or para-position relative to the amino group in Ar; and when n is equal to or greater than 2, R and $R_1$ respectively represent two or more substituents which are the same or different, wherein said solid acid catalyst consists of an H-type beta zeolite and an active alumina, the molecular ratio of $SiO_2/Al_2O_3$ in the H-type beta zeolite is between 20 and 100, and the content of the active alumina is between 10% and 70% (wt).

2. The process according to claim 1, wherein in said solid acid catalyst, the molecular ratio of $SiO_2/Al_2O_3$ in the H-type beta zeolite is between 30 and 70, and the content of the active alumina is between 20% and 50% (wt).

3. The process according to claim 1, wherein said diarylamine is diphenylamine.

4. A process for preparing diarylamines from arylamines, said process comprising reacting a compound of formula (I):

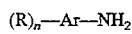  (I)

with a compound of formula (II):

  (II)

in the presence of a solid acid catalyst at a temperature between 250° and 450° C. to obtain a diarylamine compound of formula (III):

  (III)

wherein

R and $R_1$ are identical or different, and each represents $C_{1-12}$ alkyl, $C_{1-12}$ alkoxy, $C_1$ alkoxy $C_{1-12}$ alkyl, hydroxy $C_{1-12}$ alkyl, phenyl, phenyl $C_{1-12}$ alkyl, hydroxy, amino or nitro;

Ar represents phenyl;

n represents an integer from 0 to 5, when n is 1, R and $R_1$ are in the ortho-, meta- or para-position relative to the amino group in Ar; and when n is equal to or greater than 2, R and $R_1$ respectively represent two or more substituents which are the same or different, wherein said solid acid catalyst consists of an H-type beta zeolite and an active alumina, the molecular ratio of $SiO_2/Al_2O_3$ in the H-type beta zeolite is between 20 and 100, and the content of the active alumina is between 10% and 70% (wt), wherein said solid acid catalyst is prepared by a process comprising the steps of:

mixing an H-type beta zeolite with 10 to 70% by weight of Al(OH)$_3$ powder based on the γ-Al$_2$O$_3$ content in the catalyst;

adding a suitable amount of dilute nitric acid to form a mixture;

mixing and kneading the mixture to form a homogeneous mixture;

extruding the homogeneous mixture to form strips;

drying the strips at 60° C. for 4 to 8 hours and at 110° to 120° C. for 4 to 8 hours; and calcining the strips at 500° to 700° C. for 8 to 16 hours.

* * * * *